United States Patent [19]

Patel

[11] 4,195,057
[45] Mar. 25, 1980

[54] VAPOR-PHASE MOVING-BOUNDARY INDICATOR

[75] Inventor: Gordhanbhai N. Patel, Morris Plains, N.J.

[73] Assignee: Allied Chemical Corporation, Morris Township, Morris County, N.J.

[21] Appl. No.: 938,173

[22] Filed: Aug. 30, 1978

[51] Int. Cl.² .......................................... G01N 21/06
[52] U.S. Cl. .................................. 422/56; 23/230 R; 422/58; 116/206
[58] Field of Search ................ 23/230 R; 422/56, 57, 422/86, 58; 116/114 AM, 114 V; 73/358

[56] References Cited

U.S. PATENT DOCUMENTS

| | | | |
|---|---|---|---|
| 3,501,297 | 3/1970 | Cremeans | 96/48 |
| 3,615,719 | 10/1971 | Michel et al. | 73/358 |
| 3,768,976 | 10/1973 | Hu et al. | 116/114 V |
| 3,844,718 | 10/1974 | Cohen | 23/253 TP |
| 3,999,946 | 12/1976 | Patel et al. | 23/253 TP |
| 4,042,336 | 8/1977 | Larsson | 73/358 |

*Primary Examiner*—R. E. Serwin
*Attorney, Agent, or Firm*—Robert J. North; Gerhard H. Fuchs

[57] ABSTRACT

An improved vapor-phase moving-boundary indicator is described, which is useful for monitoring the time-temperature histories of perishables. The device functions by allowing a vapor to permeate through a porous substrate contacted with a solution of a polydiacetylene indicating compound wherein the solution undergoes a color change upon contact with the vapor. As the vapor permeates through and along the substrate, a visible moving boundary is created between two colors which advances as a function of time and temperature. This provides a visual record of the integrated time-temperature exposure of the article.

9 Claims, 4 Drawing Figures

VAPOR-PHASE MOVING-BOUNDARY INDICATOR

BACKGROUND OF THE INVENTION

1. Field of the Invention

This invention relates to a device for monitoring the time-temperature history of an article in which a vapor is allowed to permeate through a porous substrate contacted with a solution of a polydiacetylene indicating compound in a suitable solvent, which undergoes a color change upon contact with the vapor, thus forming a moving boundary as vapor permeates through the substrate.

2. Brief Description of the Prior Art

A host of perishable products such as frozen foods, blood, vaccines and the like require a means for monitoring time temperature shelf-life histories. Various indicators have been described in the prior art as meeting this need with varying success.

Indicators are known that use a liquid or liquid vapor for activating a color response when a predetermined shelf life has expired. For example, U.S. Pat. No. 3,844,718 discloses a defrost indicator which is activated by the contact of water or water vapor with a water-soluble ink supported on a hydroscopic substrate.

U.S. Pat. No. 3,768,976 discloses a time-temperature indicator that depends upon the rate of permeation of oxygen through a polymer envelope containing an aqueous solution of a red redox dye. Upon oxidation, the red dye turns colorless, indicating that the perishable has been exposed to too high a temperature for too long a time.

U.S. Pat. No. 3,915,719 discloses a temperature indicator in which a frozen liquid is separated from an indicating layer by a liquid-soluble barrier. When the frozen liquid thaws, a time delay is introduced by the rate of dissolution of the liquid soluble barrier. Only upon dissolution of this barrier does color indication occur.

U.S. Pat. No. 3,501,297, discloses a mixture of diacetylenes, irradiated by ultraviolet radiation producing a blue-bronze color, capable of being converted by contact with warm ethanol vapors to a red color. However, such a color change by itself, is insufficient to suggest application as a practical time-temperature history indicator, since the color change may simply indicate that a particular temperature has been exceeded, without an indication either of the length of time that temperature has been exceeded or of the time-averaged exposure at high temperatures.

U.S. application Ser. No. 911,565 (Patel to Allied Chemical, 1978) describes a device for measuring time-temperature histories of an article in which a vapor is allowed to permeate through a porous substrate coated with an indicating solid thus producing a color response upon contacting said solid. Due to the fact that the vapor front permeates through and along the substrate, a moving boundary between two colors is created and advances as a function of time and temperature. However, total lifetimes are generally short for such devices, e.g. about a few hours to a few days and devices with longer lives are needed for monitoring articles having relatively long shelf lives.

U.S. Pat. No. 4,042,336 (1977) describes a device for monitoring time-temperature histories comprising a gas generating means, an indicator means supported on a wick, and a rate controlling means for the transmission of the gas generated to the indicator means in which it is possible to alter the time span over which the device is functional by incorporating into the wick a quantifier reactive with said gas. However, the device requires a quantifier as an integral part of the indicator system and does not mention or suggest the use of polydiacetylenes as the colorindicating material.

SUMMARY OF THE INVENTION

We have unexpectedly found that a relatively longer characteristic induction period can be created prior to the occurrence of a color response in a device containing a vapor, a chamber, a substrate in sealing contact with the chamber, and an indicating compound on the surface of the substrate, where a color response is produced upon contact of the vapor with the indicating compound, and where the vapor is constrained to permeate along and throughout the substrate prior to contacting the indicating compound. The longer characteristic induction periods are produced by providing the device with a liquid indicator, comprising a polydiacetylene indicating compound in the form of a solution.

In accordance with this invention, there is provided in a device for monitoring the time-temperature history of an article including:

(a) a closed vapor-impermeable container;

(b) a chamber forming one portion inside of said container;

(c) an adsorptive substrate, through which vapor can permeate at measurable rate, having an indicating compound deposited on at least the outer surface thereof, said compound capable of undergoing a color response upon contact with vapor or condensed vapor specified below, and said substrate positioned inside said chamber such that the outer surface of said substrate, containing said compound, is in sealing contact with a portion of the inner surface of said chamber;

(d) a source of vapor, reactive with said compound to produce a color response, within said chamber, said vapor being capable of traveling through the substrate by permeation thereof, and being constrained by said sealing contact to contact said substrate, as only one portion of the observable surface of said substrate prior to traveling through said substrate in order to contact said compound on the surface of the substrate; and (e) means for providing said vapor at a given moment to the chamber; whereby a moving colored boundary is produced on the surface of the substrate during travel of the adsorbed vapor throughout the substrate, the improvement which comprises providing a polydiacetylene as said indicating compound in the form of a solution, in a solvent therefor, said solution being capable of exhibiting a visual color response upon contact with said vapor, and said vapor being soluble in said solution.

Further provided, is a process for monitoring the time-temperature history of an article comprising applying to the article the improved device of this invention and providing vapor to contact said vapor-permeable barrier in the device at the beginning of the monitoring.

Also provided is an article having the improved device of this invention attached thereto.

DESCRIPTION OF THE INVENTION AND PREFERRED EMBODIMENTS

The invention device basically includes the elements of a container, a chamber which is positioned inside the container, an indicator assembly situated inside the chamber and a vapor source. By the term "indicator assembly" as used herein is meant the combination comprising substrate 5 wetted with solution 6 of the polydiacetylene indicating compound. By the term "liquid indicator" as used herein is meant the combination of polydiacetylene indicating compound in a solvent therefor, i.e., solution 6. The prior art device comprises an indicator assembly positioned inside the chamber in sealing contact with a portion of the inner surface of the chamber such that vapor is constrained to permeate through the indicator assembly comprising a substrate having an indicating compound deposited thereon, to contact the indicating compound at only one portion of the observable surface of the indicator assembly thereby producing a color response. As the vapor permeates longitudinally through the length of the indicator assembly, the color response takes the form of a moving boundary. In contrast to the above prior art device, described in U.S. application Ser. No. 911,565, the improved device of this invention utilizes the indicating compound, a polydiacetylene, in the form of a solution, wherein longer total lifetimes are obtainable.

Figure 1:
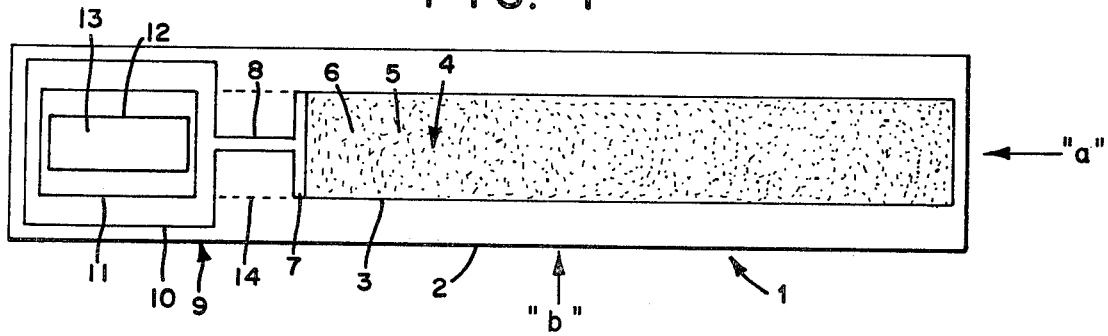
FIG. 1 is an illustration of the top view of one modification of the basic invention device showing substrate 5 positioned in sealing contact inside of chamber 3.
Figure 3:
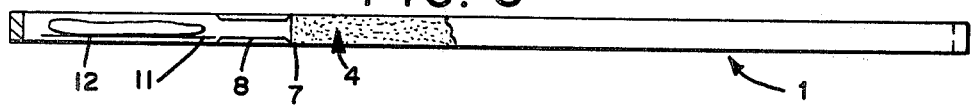
FIG. 3 is a side view of the above device from the position "b", as designated in FIG. 1.
Figure 2:
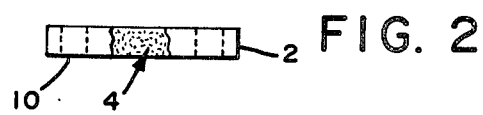
FIG. 2 is an end view of the above device from position "a", designated in FIG. 1.

A description of a preferred embodiment of the invention device can be readily made by reference to FIG. 1, FIG. 2 and FIG. 3. Device 1 comprises a vapor-impermeable container 2, in which is housed indicator assembly 4, comprised of an adsorptive substrate 5, wetted with solution 6 containing dissolved indicating compound. Said indicator assembly is housed in indicator chamber 3, and positioned in such a manner that said substrate 5 of indicator assembly 4 is flush against the inner surface of chamber 3 forming sealing contact 7. Vapor-entry chamber 8 connects indicator chamber 3 with vapor source 9 which comprises vapor chamber 10, evaporation substrate 11, solvent reservoir 12 and solvent 13.

Device operation comprises initially rupturing the frangible solvent reservoir 12, as for example, by hand pressure to release solvent into the system. This action is designated as the starting point of the monitoring process. As solvent 13 is released from reservoir 12, it contacts evaporation substrate 11 and is absorbed. Evaporation of solvent from the substrate forms vapor which can contact the indicator assembly 4. Formed vapor travels through vapor chamber 10, through vapor-entry chamber 8 and arrives at the indicator assembly at sealing point 7. Due to the fact that sealing point 7 prevents vapor from diffusing around the sides of substrate 5, it is constrained to contact only one portion of the observable surface of the substrate and to permeate through adsorptive substrate 5. While said vapor permeates through substrate 5, it permeates to the surface of said substrate and contacts solution 6 of indicating compound, which then exhibits a color response, usually being a color change. Since substrate 5 is wetted with solution 6, diffusion of vapor through substrate 5 is slower in comparison to a dry substrate of the device described in U.S. application Ser. No. 911,565. As the vapor travels the length of substrate 5, a corresponding color response occurs on the surface of the substrate and thus the vapor-transport creates a colored moving boundary. The rate of travel of the moving boundary between two selected points on the surface of the substrate can be regulated by suitable choice of vapor, adsorptive substrate 5 and solution 6 of indicating compound, such that the time required for the boundary to travel between the points corresponds to a predetermined time-temperature history of an article at a particular temperature such as the shelf-life of the article.

Knowledge of the time required for the moving boundary to travel between two points on the surface of the substrate at a particular temperature, for a device of known geometry and vapor-indicator combination, allows the time of thermal annealing to be monitored at known temperature, or conversely, the temperature to be monitored during a known time interval.

The device of this invention can be used for monitoring the time-temperature histories of perishable products over a temperature range of about $-70°$ to $+150°$ C. and from times ranging from about 1 minute to one year, depending on the choice of vapor, and indicator, which will be obvious to one skilled in the art from the disclosure herein. The device can be utilized in a variety of ways including attaching the device to the article to be monitored by means of an adhesive-type backing on the container or by placing the device in close proximity to the article in the area in which it is being stored, for instance on the inside of a cabinet door, or on a wall or shelf of the storage facility.

The function of the sealing contact is to create a characteristic rate of travel for the moving boundary and a characteristic activation energy for such travel rate, such that the time required for the moving boundary to travel between two predetermined points on the liquid surface of the substrate of the indicator assembly can be predictably controlled as a function of temperature.

The sealing contact in the device must be positioned between the vapor and indicator assembly such that the vapor is constrained to contact only one portion of the observable surface of the substrate and to permeate through the substrate prior to contacting the solution of indicating compound such that the color response does not occur simultaneously with release of vapor to the system. In addition, the adsorptive substrate must be measurably permeable to said vapor and must not be dissolved by said vapor during the monitoring period. However, a slight swelling effect of the adsorptive substrate may occur during the monitoring, and may be tolerated provided that reproducible kinetics can be obtained for boundary movement.

By the term "sealing contact" is meant the state of the juncture between the outer longitudinally exposed surface of the substrate and the inner surface of the indicator chamber in which the indicator assembly is positioned. The degree of contact between the outer surface of the substrate and the inner surface of the chamber must be such that vapor is not allowed to contact the entire observable surface of the substrate simultaneously, and to travel between the inner surface of the chamber and the outer surface of the substrate. This can be accomplished in a variety of ways such as choosing a substrate of such volume and geometry as to "snugly" fit the inside volume of the chamber to form the sealing contact. Alternately, the substrate can be glued or adhered to the inner surface of the chamber by a suitable adhesive, which must not be soluble or chemically reactive toward the vapor used in the device. It is preferred, however, to shape the indicator chamber to the volume and geometry of the substrate, in that portion of the indicator chamber in which the substrate is to be positioned. This is usually accomplished by "sealing" the container material around the substrate to obtain a tight fit and maximum contact between substrate and chamber.

In referring to the rate of travel of the moving boundary, the term "moving boundary rate" is used herein. By the term "energy of activation of the system" is meant the value of $E_{act.}$, obtained by measuring the moving boundary rate during device operation at two or more temperatures. The logarithmic time required for the boundary to move a certain distance, ($\ln t$), as the ordinate is plotted versus the inverse absolute temperature, $1/T$, as the abscissa and the $E_{act.}$ energy of activation is calculated from the slope of the resulting straight line curves, by known methods in the art.

The moving boundary rate is characteristic for a particular device of a particular geometry and a particular vapor-liquid indicator combination. Thus, devices having identical geometries and vapor-liquid indicator combinations will possess substantially identical moving boundary rates at identical temperatures.

The container of the device is a closed vapor-impermeable structure housing the vapor source, indicator chamber and indicator assembly of the device. The container operates to prevent any vapor from escaping out of the device and also to provide an observable view of the developing moving boundary during the monitoring period. Representative examples of suitable materials for constructing the container include polyethylene, polypropylene, polyester, such as polyethylene and polybutylene terephthalates, and polyamide, such as nylon 66. A preferred material is polyester.

In addition, the container may also have an adhesive backing to allow a means for attaching the device to an article to be monitored.

A further embodiment includes a "masking portion" on the front (top) of the device containing a small "window" at one point of the indicator assembly. Operation of the device is conducted wherein the device is calibrated such that a particular monitoring period at a predetermined temperature will cause the moving boundary to appear in the window, thus signalling a "go-no go" situation in which the monitoring period has expired.

The size and design of the container can be varied to suit the particular article to be monitored. A limitation on the size of the device is that it must be large enough to exhibit an observable color response under the conditions of monitoring.

The chamber of the device is a portion of the inside of the container which acts as a holder for the indicator assembly and also through which the moving boundary can be observed. The chamber, also referred to as the "indicator chamber", is generally formed by shaping the chamber material to fit the longitudinally exposed surface of the substrate. The chamber can be of any vapor-permeable material such as polyethylene, polypropylene, polyester, such as polyethylene and polybutylene terephthalates, and polyamide, such as nylon 66.

It is preferred to use the container material in constructing the chamber.

The indicator chamber is connected to the vapor source by means of a vapor-entry chamber as illustrated in FIG. 1. This particular chamber can be constructed of materials used for the container and indicator chamber as described above. It is preferred to use the same material as that used for the indicator chamber. As illustrated in FIG. 1, chamber 8 is narrow, which acts to increase the time required for vapor to reach and contact the indicator assembly. Alternately, a wider vapor-entry chamber can be utilized such as chamber 14 in FIG. 1, which is outlined by dotted lines.

The indicator assembly of the device must be capable of exhibiting a visual color response upon contacting a vapor, permeating along and throughout the surface of the substrate indicator assembly to contact the solution of indicating compound deposited thereon, at least the outer observable surface thereof. Upon contact with said vapor, or condensed vapor, the liquid indicator undergoes a color response, preferably a color change, which moves on the surface of the substrate as a boundary between differently colored regions as vapor travels through said indicator assembly. The reason as to why the solution of polydiacetylene indicating compound undergoes a color response upon contacting with said vapor is not clearly understood and may be due to a variety of mechanisms such as precipitation of the indicating compound from solution, production of a new conformation of said indicating compound in solution, production of a differently hydrogen-bonded species of said compound in solution, or the like. Regardless of the mechanism underlying the color response, the incorporation of a vapor-liquid indicator combination into the device system is not specifically directed or predicated upon one particular mechanism, but is based generally upon the observed fact that a solution of an indicating compound is capable of undergoing a color response upon contact with a vapor or condensed vapor and capable of forming a visual moving boundary.

The total lifetime for the device of this invention is lengthened by the use of a liquid indicator system, in which a solution of indicating compound in a suitable solvent is contacted with a substrate. The reason why the total lifetime for the device in this improved modification is lengthened over the induction period of the prior art utilizing a solid indicator system is not clearly understood. The answer may be that a higher concentration of diffusing vapor is required for a color transition in the present liquid indicator system.

The indicator assembly comprises a solution of an indicating compound absorbed and deposited on an adsorptive substrate, which provides the indicating compound in solution form to the device. The substrate can be any solid vapor-permeable material which acts as a support for the solution and a means of transport for the vapor, by adsorption during the monitoring process, in which the rate of transport can be measured. The liquid indicator is deposited on at least the outer observable surface thereof.

Representative examples of the adsorptive support are filter paper, cotton and wool. Preferred material used as the adsorptive substrate is filter paper. Size and volume of the adsorptive substrate will vary with the intended application and will be obvious to one skilled in the art. Shape of said substrate can be flat, rectangular or cylindrical. Preferred is a flat shape since a larger observable exposed surface is possible.

The solution of indicating compound can be deposited on the adsorptive substrate by conventional means.

The solution of indicating compound is dispersed on the surface of the adsorptive substrate and as a result may also permeate into the internal matrix of the support. However, only the exposed surface of the indicator assembly is available for use in monitoring time-temperature histories.

The solution of indicating compound may be uniformly dispersed over the surface of the substrate or may be placed at various intervals along the length of the porous substrate which correspond to certain predetermined time periods at a given temperature. Thus, such a device can operate wherein a "visible moving boundary" is not created continuously during the monitoring period, but only appears as the "end-point" of the measuring period.

The indicating compounds of the improved invention device are polydiacetylene compounds, or mixtures thereof, formed from diacetylene monomers containing at least one conjugated diyne group (i.e., —C≡C—C≡C—) per molecule. Polydiacetylene compounds are known in the art, including methods of preparation, and are adequately described in U.S. Pat. No. 3,999,499 (Patel et al. to Allied Chemical, 1976) which is hereby incorporated by reference. The polydiacetylene compounds typically contain at least one substituent (R or R' below) selected from the group consisting of alkyl, aryl, sulfonate, urethane and alcohol derivatives and preferably the polydiacetylene contains two urethane substituents. Representative examples include those of the formula:

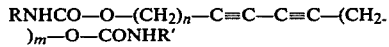

RNHCO—O—(CH$_2$)$_n$—C≡C—C≡C—(CH$_2$)$_m$—O—CONHR' where n and m are integer values and can be the same or different and are at least 1, and preferably 1–4; and wherein R and R' can be the same or different and are alkyl, aryl, sulfonate, urethane and alcohol derivatives.

Representative polydiacetylenes of the above formula useful in the instant invention include those formed from monomers in the listing below where n=m, R=R' and descriptive shorthand chemical names are given:

| n,m | R,R' | Descriptive Name |
|---|---|---|
| 2 | C$_2$H$_5$ | ODEU |
| " | meta chlorophenyl | ODDmCPU |
| " | (CH$_2$)$_3$CH$_3$ | ODDnBU |
| 3 | CH$_3$ | 3DMU |
| " | ortho chlorophenyl | 3DoCPU |
| " | phenyl | 3DPU |
| " | C$_2$H$_5$ | 3DEU |
| 4 | CH$_3$ | 4DMU |
| " | C$_2$H$_5$ | 4DEU |
| " | -CH$_2$CH$_2$Cl | 4D2CEU |
| " | ortho chlorophenyl | 4DoCPU |
| " | meta methoxyphenyl | 4DmMPU |
| " | para chlorophenyl | 4DpCPU |
| " | meta tolyl | 4DmTU |

Preferred polydiacetylenes in the invention are those produced from monomeric diacetylenes wherein R and R' independently have the formula:

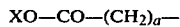

XO—CO—(CH$_2$)$_a$— wherein X is linear or branched C$_1$–C$_{18}$ alkyl; and a is an integer value from 1–5. Particularly preferred polydiacetylenes are those derived from diacetylenes of the above formula wherein m and n are the same and either 3 or 4; a is one; and R and R' are the same and X is either ethyl or n-butyl. Representative examples of this class are: 4,6-decadiyn-1,10-diol bis(ethoxycarbonylmethylurethane), 3 DECMU, 4,6-decadiyn-1,10-diol bis(n-butoxycarbonylmethylurethane), 3 DBCMU, 5,7-dodecadiyn-1,12-diol bis(ethoxycarbonylmethylurethane), 4 DECMU, 5,7-dodecadiyn-1,12-diol bis(n-butoxycarbonylmethylurethane), 4DBCMU.

Solvents for the indicating compounds of this invention include those which are good solvents for the compounds, are chemically inert under the conditions of the monitoring, don't significantly dissolve the materials of construction of the container and has a boiling point of at least about 25° C. or higher at atmospheric pressure. Representative examples of classes of solvents include C$_3$–C$_6$ alkyl ketone, halogenated C$_1$–C$_4$ alkane, containing 1 to 4 halogen atoms, C$_3$–C$_6$ N,N-dialkylalkanoamide, C$_1$–C$_3$ monohydric alkyl alcohol, C$_1$–C$_5$ saturated alkanoic monocarboxylic acid, or lower alkyl ester thereof, C$_1$–C$_4$ nitroalkane, C$_2$–C$_6$ alkyl sulfoxide, C$_2$–C$_6$ alkyl ether, cyclic C$_4$–C$_6$ alkyl ether, C$_7$–C$_9$ alkylphenol, C$_5$–C$_{10}$ heterocyclic nitrogen compounds, phenol, water, equivalents or mixtures thereof. Specific examples include methyl ethyl ketone, dichloromethane, chloroform, carbon tetrachloride, dimethyl sulfoxide, N,N-dimethylformamide, N,N-dimethylacetamide, methanol, ethanol, isopropanol, acetic acid, water, p-dioxane, p-cresol, phenol, pyridine, ethyl acetate, nitromethane, dimethylsulfoxide, trifluoroacetic acid and trifluoroethanol.

Preferred solvents are chloroform, acetone, trifluoroacetic acid and trifluoroethanol.

In general, solutions of indicating compound in solvent of about 0.01 to about 50 percent compound by weight of solution are used and preferably solutions of about one percent compound by weight of solution are used.

The liquid indicators display a variety of color change when contacted with a vapor. For example, a 1 weight percent solution of poly 3DECMU in dimethylformamide is yellow and turns to a blue color upon contacting chloroform or acetone vapor. Conversely, a blue solution of poly 3DBCMU in chloroform/hexane solution turns yellow upon contact with trifluoroacetic acid. Both types of color responses can be utilized in the invention device for monitoring time-temperature histories of articles.

Vapor in the present invention device is stored as a condensed liquid, as a source of vapor, and is positioned such that upon release, formed vapor is constrained to permeate through the adsorptive substrate before contacting the solution of indicating compound. The vapor must be reactive with said compound to produce a color response, must be able to permeate through the substrate without significantly dissolving said substrate, must be soluble in the solution of compound and preferably the vapor in the condensed liquid state has a boiling point of at least about 25° C., or higher at atmospheric pressure.

Vapor in the device acts to produce a color response upon contact with said liquid indicator. The mechanism of how the color response occurs is not clearly understood and is probably different depending upon the particular vapor used. For example, as described above, poly 3DECMU in DMF solution, when contacted with chloroform or acetone, which are known non-solvents for poly 3DECMU, results in a solution color change from yellow-to-blue. Formation of intermediate conformational structures having different solubilities and colors may be involved. Conversely, a solution of poly 3DBCMU in chloroform/hexane, when contacted with a halogenated alkanoic acid, trifluoroacetic acid, a known strong hydrogen-bonding agent, results in a color change from blue to yellow. The color change here is thought to be due to the interference in the intramolecular hydrogen-bonding of the compound in solution, causing new hydrogen-bonded structures which exhibit a different characteristic long wavelength absorption and thus, a different observed color. By the term "non-solvent" as used herein is meant that the dissolved compound can be precipitated by contacting vapor of the non-solvent with the indicating solution.

Representative examples of vapor useful in the instant invention include $C_3$-$C_6$ linear or branched acyclic alkyl ketones; halogenated $C_1$-$C_3$ alkanes, containing 1-4 halogen atoms being fluorine, chlorine, bromine, iodine or mixtures thereof; halogenated $C_1$-$C_3$ alkanoic acids, containing 1-4 halogen atoms being fluorine, chlorine, bromine, iodine or mixtures thereof; $C_3$-$C_6$ N,N-dialkylalkanoamides, wherein said alkyl groups may be the same or different and may be linear or branched; $C_1$-$C_3$ monohydric alkyl alcohols; $C_1$-$C_4$ saturated alkanoic monocarboxylic acids, wherein said alkane portions may be either linear or branched; $C_2$-$C_6$ alkyl sulfoxides and $C_2$-$C_6$ alkyl ethers, wherein said alkyl groups may be the same or different and may be linear or branched; cyclic $C_4$-$C_9$ alkyl ethers, said alkyl groups being either linear or branched; $C_7$-$C_9$ alkylphenols, said alkyl groups being either linear or branched and said phenol being either mono-, di- or trisubstituted; $C_5$-$C_{10}$ heterocyclic nitrogen compounds, containing up to 2 ring nitrogen atoms, and 1 or 2 aromatic rings, being fused or separated; phenol, trihaloacetic acids, water, equivalents of the above-recited compounds or mixtures thereof. Preferred vapors for use in the invention device are those which act as a non-solvent for the compound in solution, or as a hydrogen-bonding agent for the compound in solution. Vapors which satisfy these criteria will be obvious to one skilled in the art from this disclosure. Illustrative of particular preferred vapors are acetone, methyl ethyl ketone, dichloromethane, chloroform, carbon tetrachloride, dimethylsulfoxide, dimethylformamide, dimethylacetamide, methanol, ethanol, isopropanol, acetic acid, water, p-dioxane, p-cresol, phenol, pyridine, trifluoroacetic, trichloroacetic acid, equivalents or mixtures thereof.

Means for providing vapor to the container, at the beginning of the monitoring process is positioned inside the container and comprises a frangible solvent reservoir, containing solvent, and supported on an evaporation substrate, said means connected to the vapor-entry chamber, which is in turn connected to the indicating chamber. The reservoir being frangible, it is easily ruptured, as for example, by hand pressure at the beginning of the monitoring period. The solvent is allowed to vaporize from a wetted evaporation substrate, e.g., a porous substrate, such as filter paper, which facilitates evporation. The solvent reservoir can be constructed of a variety of materials with the proviso that the reservoir material is not significantly soluble in the solvent, but may be slightly swelled during the monitoring process. In one embodiment, the material is sufficiently non-permeable to the solvent that escape of solvent to the ontainer does not occur prior to the desired monitoring period. Representative materials that can serve as the solvent reservoir include thin walled glass, and frangible but vapor-impermeable plastic. A preferred material is glass.

A preferred device of the invention is wherein liquid indicator is comprised of: poly[4,6-decadiyn-1,10-bis(ethoxycarbonylmethylurethane), poly 3DECMU, as indicating compound, dissolved in dimethylformamide, absorbed and deposited on filter paper as the adsorptive substrate, and wherein the vapor is chloroform, acetone, or trifluoroacetic acid.

Also provided in the instant invention is a process for monitoring the time-temperature history of an article comprising applying to the article the improved device of this invention and providing vapor to contact the vapor-permeable barrier in the device at the beginning of the monitoring period. The device may also contain a means, by which it can be readily attached to an article to be monitored, preferably an adhesive backing. Means for providing vapor to the device are discussed hereinabove and can be a frangible solvent reservoir, as described herein, which can easily be activated by hand pressure, for example. The monitoring process can be controlled at a temperature of about $-70°$ to $+150°$ C.; at atmospheric pressures and even reduced pressures in a partial vacuum.

Also a part of the instant invention is an article having the device of the invention, as described herein, attached thereto. Such articles include frozen foods, blood plasma, perishable vaccines, photographic film and the like.

The nature of the container, chamber, indicator assembly, solution of indicating compound, substrate, vapor and means for providing vapor to the device are fully and adequately described hereinabove. The device indicator assembly can be prepared by contacting the adsorptive substrate with a solution of the indicating compound such as by immersion. Alternately, the indicating compound may be dispersed in a medium such as a binder and applied to the substrate. The indicator assembly can then be positioned inside the chamber, in sealing contact therewith, by means of a sealer, such as a hot press sealer, hot air sealer and pressure sensitive adhesives. Preferred is a hot press sealer. The other components of the device including the vapor source solvent reservoir and evaporative substrate, are also sealed in the container by means of the sealer to form the completed device.

The following examples are illustrative of the best mode of carrying out the invention, as contemplated by , but should not be construed to be limitations on the scope or spirit of the instant invention. Parts are by weight where given unless otherwise indicated.

EXAMPLE 1

PREPARATION AND USE OF THE VAPOR PHASE MOVING BOUNDARY INDICATOR

1. Preparation of the Device

A device similar to that illustrated in FIG. 1 was prepared. The indicator assembly in each device was prepared by wetting a 0.6 cm. × 5 cm. strip of Whatman No. 1 filter paper with a yellow solution of 1 weight percent poly 3 DECMU in dimethylformamide. The strip was then firmly encased and sealed on three sides in a piece of 4.5 mil thick polyethylene terephthalate polyester. Next, a 0.5 × 1.5 cm piece of filter paper saturated with chloroform was placed into the other end of the chamber and the entire assembly quickly sealed by means of a hot sealer.

2. Description of the Runs

Figure 4:
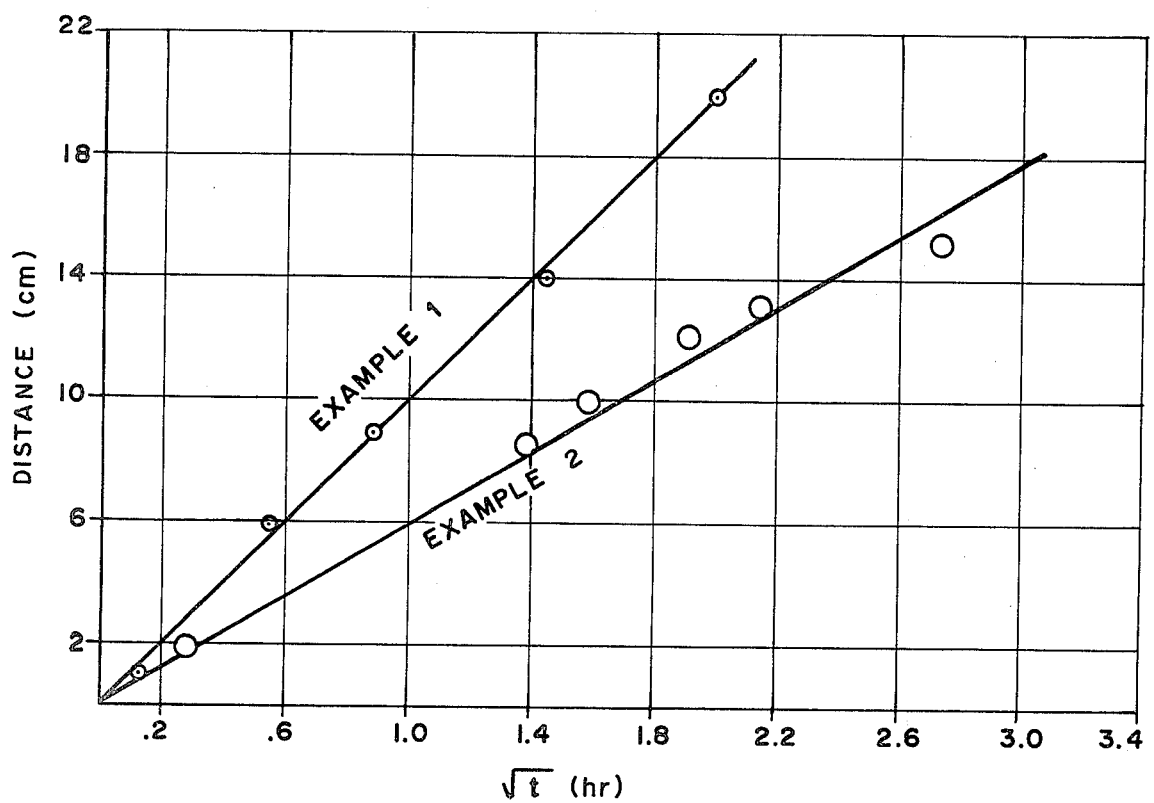
FIG. 4 is a composite plot of distance travelled by the moving boundary vs. $t^{\frac{1}{2}}$, the square root of the time required to travel that distance for the devices of Examples 1 and 2.

The beginning of the measurement, i.e., the development of the colored moving boundary, was taken when the entire system was sealed and vapor began to diffuse into the color indicating strip at room temperature. Upon contact with vapor the yellow indicating solution turned blue and at that point, formed a yellow-blue boundary. As the vapor permeated through and along the indicating strip, the boundary moved correspondingly, thus forming a colored moving boundary history of the time-temperature exposure. FIG. 4 illustrates the times required for the moving boundary to travel a certain distance, the square root of the required time, and the distance travelled in centimeters for the device system.

EXAMPLE 2

USE OF HYDROGEN-BONDING AGENT AS VAPOR

The device of Example 1 was used except that the indicating solution was a blue one weight percent solution of poly 3DBCMU in chloroform/hexane solution and the vapor used was trifluoroacetic acid. Device operation was conducted at room temperature and the results are illustrated in FIG. 4 wherein the experimental data on rate of advancement of the formal yellowblue colored boundary along the indicator strip is illustrated.

I claim:

1. In a device for monitoring the time-temperature history of an article including
  (a) a closed vapor-impermeable container;
  (b) a chamber forming one portion inside of said container;
  (c) an adsorptive substrate, through which vapor can permeate at measurable rate, having an indicating compound deposited on at least the outer surface thereof, said compound capable of undergoing a color response upon contact with vapor or condensed vapor specified below, and said substrate positioned inside said chamber such that the outer surface of said substrate, containing said compound, is in sealing contact with a portion of the inner surface of said chamber;
  (d) a source of vapor, reactive with said compound to produce a color response, within said chamber, said vapor being capable of traveling through the substrate by permeation thereof, and being constrained by said sealing contact to contact said substrate at only one portion of the observable surface of said substrate prior to traveling through said substrate in order to contact said compound on the surface of said substrate; and
  (e) means for providing said vapor at a given moment to the chamber; whereby a moving colored boundary is produced on the surface of the substrate during travel of the adsorbed vapor throughout the substrate, the improvement which comprises providing a polydiacetylene as said indicating compound in the form of a solution, in a solvent therefor, said solution being capable of exhibiting a visual color response upon contact with said vapor, and said vapor being soluble in said solution.

2. The improvement according to claim 1 wherein said polydiacetylene is formed by polymerizing a monomer of the following formula:

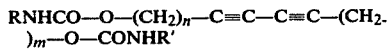

where n and m are integer values and can be the same or different and are at least 1, and wherein R and R' can be the same or different and are selected from the group consisting of alkyl, aryl, sulfonate, urethane and alcohol derivatives.

3. The improvement according to claim 2 wherein said R and R' radicals independently have the formula:

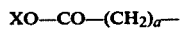

wherein X is linear or branched $C_1$–$C_{18}$ alkyl, and a is an integer value from 1–4.

4. The improvement according to claim 3 wherein said polymer is characterized in that m and n are the same and either 3 or 4; a is one; and R and R' are the same and X is either ethyl or n-butyl.

5. The improvement according to claim 1 wherein said solvent has a boiling point of at least about 25° C. at atmospheric pressure.

6. The improvement according to claim 1 wherein said solution contains about 0.01 to about 50 percent by weight of said compound.

7. The improvement according to claim 1 wherein said vapor is a non-solvent for the compound in solution.

8. The improvement according to claim 1 wherein said vapor is a hydrogen-bonding agent for the compound in solution.

9. A process for monitoring the time-temperature history of an article comprising applying to the article the device of claim 1 and providing vapor to contact said vapor-permeable barrier in the device at the beginning of the monitoring.

* * * * *